United States Patent [19]

Spears

[11] Patent Number: 5,407,426
[45] Date of Patent: * Apr. 18, 1995

[54] METHOD AND APPARATUS FOR DELIVERING OXYGEN INTO BLOOD

[75] Inventor: James R. Spears, Bloomfield Hills, Mich.

[73] Assignee: Wayne State University, Detroit, Mich.

[*] Notice: The portion of the term of this patent subsequent to Nov. 16, 2010 has been disclaimed.

[21] Appl. No.: 152,589

[22] Filed: Nov. 15, 1993

Related U.S. Application Data

[63] Continuation-in-part of Ser. No. 818,045, Jan. 8, 1992, Pat. No. 5,261,875, which is a continuation of Ser. No. 655,078, Feb. 14, 1991, Pat. No. 5,086,620.

[51] Int. Cl.6 ............................................. A61M 37/00
[52] U.S. Cl. .......................................... 4/24; 62/51.1; 128/898
[58] Field of Search ...................... 604/22–26, 604/269,280,282, 93, 96; 62/51.1, 78, 46.1; 128/658, 898

[56] References Cited

U.S. PATENT DOCUMENTS

| | | | |
|---|---|---|---|
| 4,450,841 | 5/1984 | Osterholm | 128/898 |
| 4,963,130 | 6/1990 | Osterholm | 604/24 |
| 5,072,739 | 12/1991 | John | 128/897 |
| 5,086,620 | 12/1992 | Spears | 62/51.1 |
| 5,261,875 | 11/1993 | Spears | 604/24 |

Primary Examiner—John D. Yasko
Assistant Examiner—Chalin Smith
Attorney, Agent, or Firm—Brooks & Kushman

[57] ABSTRACT

A method and apparatus for delivering oxygen into an environment of interest, such as blood plasma, having the characteristic of a low concentration of oxygen before delivery. The method includes the steps of preparing a mixture of oxygen and a liquid, compressing the mixture so that the oxygen dissolves in the liquid to form an oxygen-enriched liquid, delivering the oxygen-enriched liquid to a catheter having an internal diameter and length which retains the oxygen in solution and prevents the formation of bubbles, positioning the catheter in the environment of interest, and injecting the oxygen-enriched liquid into the environment through the catheter, such that the environment rapidly becomes enriched in oxygen. The apparatus includes a catheter with drawn silica tubing having narrowly defined passages through which oxygen-enriched liquid passes to oxygenate blood plasma.

27 Claims, 3 Drawing Sheets

METHOD AND APPARATUS FOR DELIVERING OXYGEN INTO BLOOD

CROSS-REFERENCE TO RELATED APPLICATIONS

This application is a continuation-in-part of my application Ser. No. 818,045 filed Jan. 8, 1992 (to issue as U.S. Pat. No. 5,261,875), which is a continuation of my application Ser. No. 655,078 filed Feb. 14, 1991 (now U.S. Pat. No. 5,086,620).

BACKGROUND OF THE INVENTION

1. Technical Field

This invention relates to a method and apparatus for delivering oxygen into an environment of interest, such as blood plasma. More particularly, the invention concerns a method and apparatus for systemic oxygenation of hypoxemic blood by intravenous injection of an aqueous suspension of oxygen in a carrier, such as water.

2. Description Of Background Art

Oxygen administration by ventilation, even at a high inspired oxygen tension, may be ineffective in potentially reversible respiratory insufficiency in a clinical setting. Such conditions include adult respiratory distress syndrome, acute pulmonary edema, foreign body aspiration, pulmonary embolism, and respiratory distress syndrome of infancy. The problem of how to treat such conditions is compounded by the pulmonary toxicity that may result from prolonged exposure to relatively high inspired oxygen tensions.

Currently, the only potentially viable medical approach for systemic oxygenation of patients calls for use of an IVOX catheter. In such devices, gas exchange occurs at the interface of a membrane of multiple small tubules and blood in the inferior vena cava. Although the potential utility of such devices has been demonstrated clinically in a small number of patients, the large size of the catheter (7-10 mm diameter) which is inserted in the femoral vein, and the large surface area presented by the tubules may result in venous thrombosis and pulmonary embolism.

In the medical field, safe and effective oxygenation of hypoxemic blood (by intravascular injection of oxygen foam or an oxygen-liberating material) has not previously been achieved. Obstruction of capillaries by surfactant-stabilized foam, inadequate mixing with blood, or liberation of toxic breakdown byproducts (including toxic oxygen moieties) of an oxygen precursor would typically occur.

Accordingly, it is an object of the present invention to provide a means for injection of oxygen into an hypoxemic medium without bubble formation or coalescence.

It is a further object of the present invention to make the size of any bubbles formed upon oxygenation so small that mixing can be achieved rapidly, whereby excessive bubble coalescence and adherence between large numbers of bubbles do not occur.

SUMMARY OF THE INVENTION

In accordance with the invention, a novel method and apparatus are disclosed for delivering oxygen into an environment of interest, such as blood plasma. The environment has the characteristic of a low concentration of oxygen before delivery.

The method comprises the steps of:
preparing a mixture of oxygen and a liquid;
compressing the mixture so that the oxygen dissolves in the liquid to form an oxygen-enriched liquid;
delivering the oxygen-enriched liquid to a catheter having an internal diameter and length which retains the oxygen in solution and prevents formation of any bubbles which could otherwise emerge from the oxygen-enriched liquid upon emergence from the catheter as a result of a pressure drop along its length;
positioning the catheter in the environment of interest; and
injecting the oxygen-enriched liquid into the environment through the catheter so that the environment is oxygenated rapidly.

Other objects and advantages of the invention will become apparent upon reading the following detailed description and upon reference to the following drawings.

BEST MODE(S) FOR CARRYING OUT THE INVENTION

Figure 1:
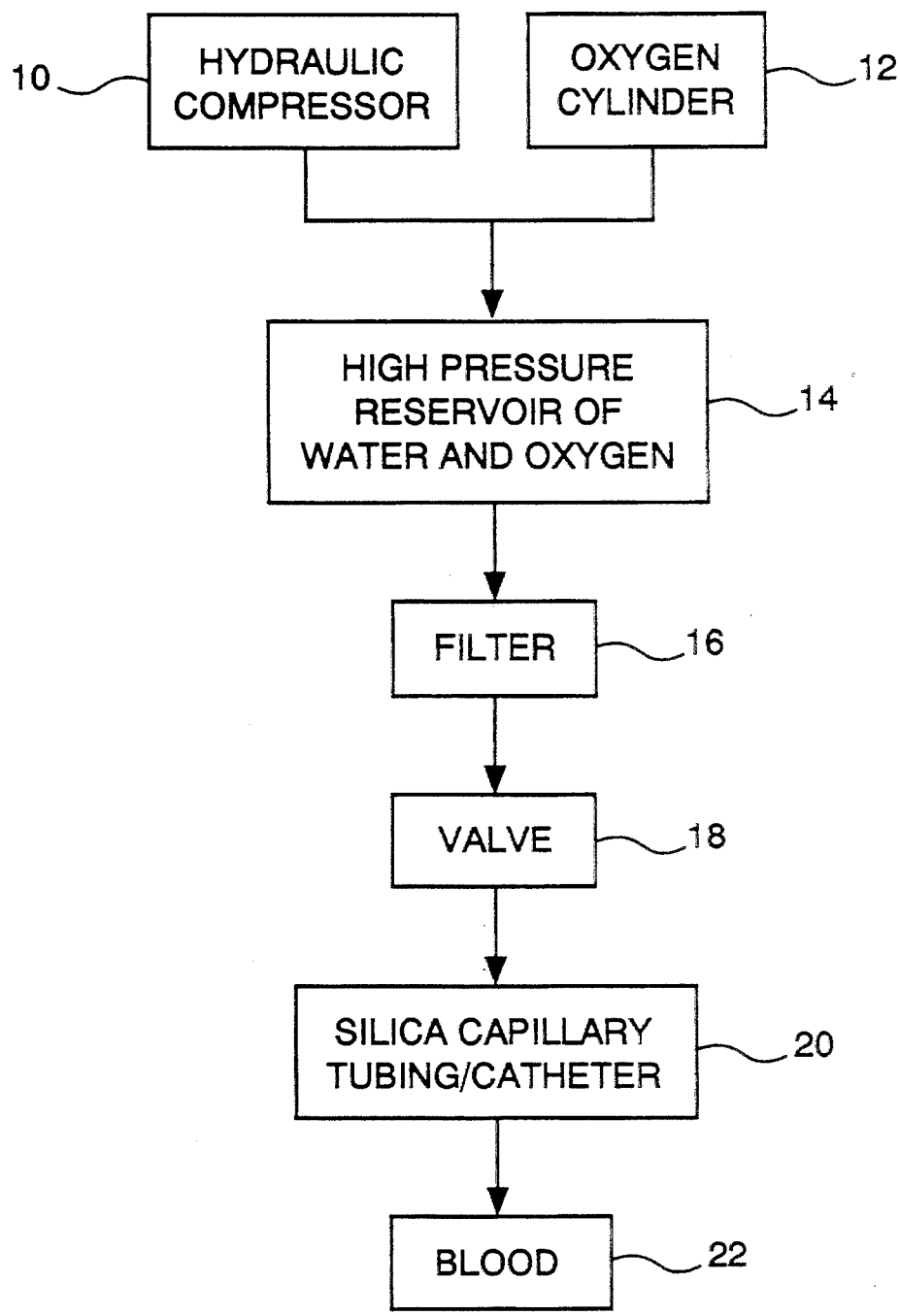
FIG. 1 is a schematic diagram of apparatus used to practice a method according to the present invention of injecting oxygen into blood plasma.
Figure 2:
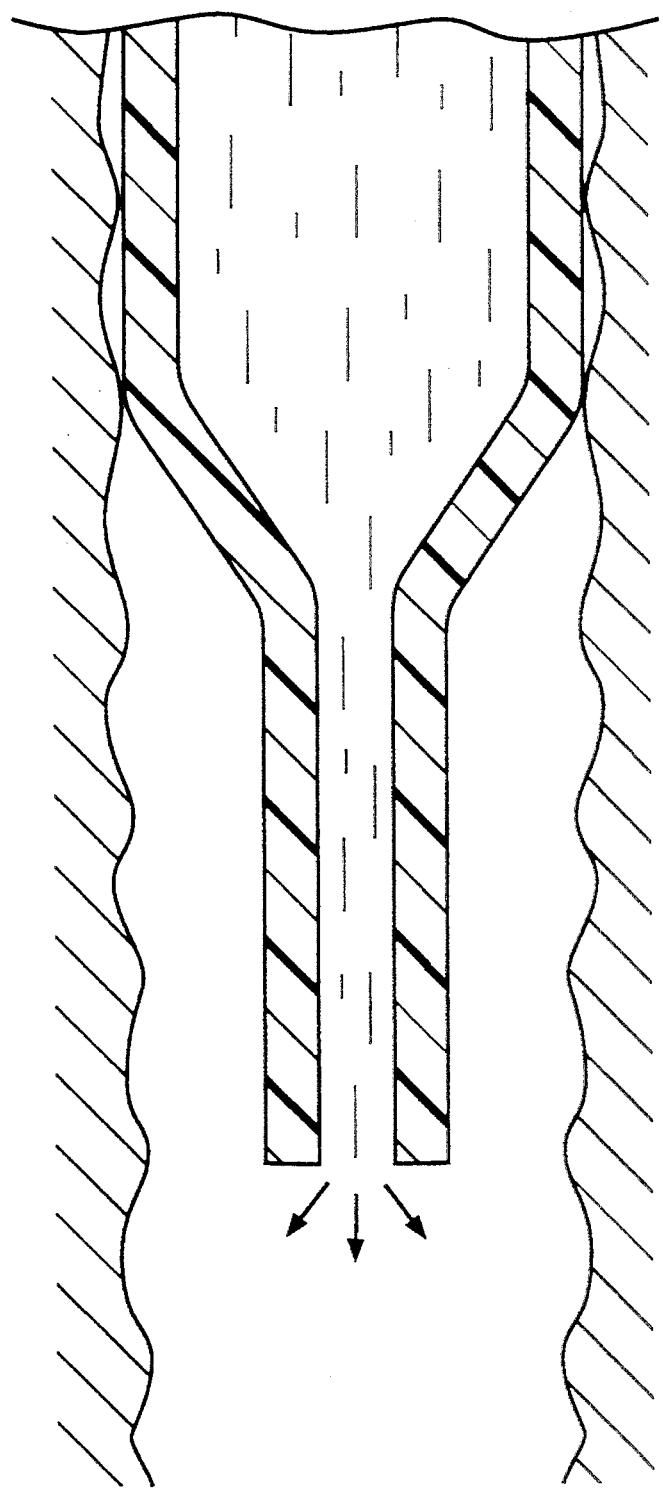
FIG. 2 is a longitudinal sectional view of a catheter constructed in accordance with the present invention.
Figure 3:
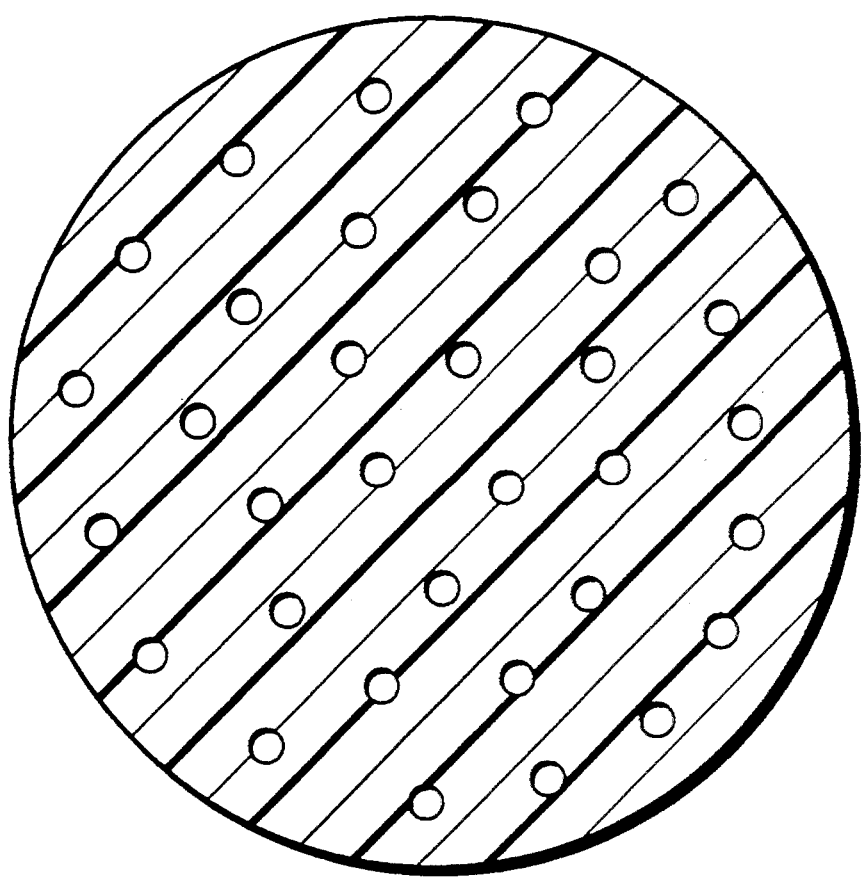
FIG. 3 is a transverse sectional view of an alternate embodiment of a catheter constructed in accordance with the present invention.

With reference to FIGS. 1-3 of the drawings, an apparatus used to practice the disclosed method includes a suitable hydraulic compressor 10 for delivering a liquid carrier (such as water) under pressure. It and and oxygen cylinder 12 are connected via suitable tubing to a high pressure reservoir 14 of the liquid carrier and oxygen. A filter 16 is in fluid communication with the reservoir 14. The filter typically has a mesh size below about 1 micron and serves to remove fine solid particles from effluents emerging from the reservoir 14. After passing through a valve 18, the effluents in the form of oxygen dissolved in water are delivered under pressure to silica capillary tubing 20 before injection into an environment of interest, such as hypoxemic blood plasma 22, via a catheter.

Also present but not depicted are suitable mechanisms for the control of temperature, pressure, and flow. I will first describe the method and then the apparatus used according to the present invention.

In greater detail, the preferred method steps for delivering oxygen into an environment of interest, such as blood plasma, having the characteristic of low concentration of oxygen before delivery, comprises the steps of:

1. Prepare a mixture of oxygen and a liquid, such as water, or a 5% solution of dextrose in water ($D_5W$);
2. Compress the mixture (in the high pressure reservoir 14) so that the oxygen dissolves in the liquid to form an oxygen-enriched liquid;
3. Deliver the oxygen-enriched liquid to a catheter having an internal diameter and length which retains at least a part of the oxygen in solution and prevents the formation of any bubbles which may emerge from the oxygen-enriched liquid upon emergence from the catheter;

4. Position the catheter in the blood plasma;

5. Inject the oxygen-enriched liquid into the oxygen-depleted environment through the catheter so that bubble formation does not occur during injection or during oxygenation of the oxygen-depleted environment.

In one series of experiments, oxygen dissolved in water (or $D_5W$ or other crystalloid) at a relatively high concentration of the gas, on the order of 3–6 cc oxygen per gram of water, can be delivered into an aqueous environment with essentially no bubble formation. Oxygen from a standard medical gas cylinder 12 was delivered to the high pressure reservoir 14 which contained water from the compressor 10. The high pressure reservoir 14 was isolated from the gas source 12. A piston was moved by the hydraulic compressor 10 to pressurize the water/oxygen mixture in the reservoir 14 to a pressure higher than needed to fully dissolve the gas, e.g., in the 1 kbar range for 3–6 cc oxygen per gram of water. After passing through appropriate filters 16, the water with the dissolved oxygen then is delivered at the same high pressure (approximately 0.5 to 1 kbar) to capillary tubing 20.

The formation of any bubbles ejected from the distal end of capillary tubing is a function of the internal diameter of the tubing. Fused silica capillary tubes (Polymicro Technology) with internal diameters ranging from 1 micron to 75 microns were tested in terms of the occurrence and size of bubbles ejected, as noted on video recordings from a light microscope.

The most critical parameter which allows an oxygen (or other gas) bubble to disappear in an aqueous environment is its size. Bubbles on the order of 3–5 microns disappear in a small fraction of a second, an observation consistent with those in the literature concerning disappearance rates of air bubbles. For example, a 2 micron bubble may disappear in 10 msec.

When fluid is ejected from the distal end of silica tubing drawn to 7 microns or less internal diameter over a ca. 1–30 mm length from a 30 micron internal diameter tubing, no bubbles were observable when the fluid was immersed under water, despite the fact that the oxygen content was as high as 5 cc gas/gm of water.

These observations suggest that it should be possible with this approach to deliver oxygen via a catheter placed in the right atrium or a great vein, without any bubble formation occurring. Therefore, problems relating to bubble formation, such as foam formation, occlusion of pulmonary capillaries, etc., would be circumvented.

In addition, it should be possible to suspend oxygen hydrate particles in initially gas-free water, without the concern for excessive hydrate decomposition or excessive diffusion of oxygen into the liquid water carrier. This is because at 0° C. (or 120 bar gas pressure, which is far exceeded by the 1 kbar hydrostatic pressure), for example, a concentration of approximately 4–5 cc oxygen in liquid water represents a point on the phase diagram equilibrium line between solid hydrate and liquid saturated with gas so the tendency of hydrate to be formed is as great as that for the hydrate to decompose.

In one experiment for delivering oxygen into blood, a hydraulic compressor (Leco/Tem-Press Div.) was used to compress a mixture of oxygen and 5% dextrose in water ($D_5W$) in a two-headed high pressure vessel. The 27 cc internal volume of the latter was initially filled with $D_5W$, with the exception that a small volume (1 to 3 cc's) was removed prior to closure of the vessel.

After closure of the vessel, the distal end of the vessel was compressed with oxygen for approximately 15 seconds via a tank of the latter at a pressure of 2500 psi. The vessel was then isolated from the oxygen source. A 3 cm long stainless steel piston, fitted with either two or three O-rings, was placed at the proximal end of the high pressure vessel, so that after closure of the vessel, pressurization with oxygen, and isolation from the oxygen source, the $D_5W$/oxygen mixture was then compressed by movement of the piston, driven by the hydraulic compressor at a pressure of 3,000 to 15,000 psi.

After allowing 10 minutes or longer for the oxygen to dissolve in the $D_5W$, a valve at the distal end of the vessel was opened to allow flow of the mixture through a 1/16" o.d./1/64" i.d. SS tubing which was connected to a hollow fused silica fiberoptic via a high pressure, low resistance filter fitted with 5 micron sintered powdered SS metal filters.

Typically, a 30 micron or 50 micron i.d. (either 363 micron or 144 micron o.d.) hollow fused silica capillary tubing (Polymicro Technologies) was used at the distal end of the delivery system, and the silica tubing was drawn at its distal end in a propane torch to an internal diameter of 1 to 10 microns over a few millimeters of axial distance. The primary resistance to flow resided at this location, and flow was therefore governed by the geometry at this location as well as by the pressure applied.

When the distal tip was submerged under degassed water, the remarkable finding was that no bubbles were observable for an oxygen concentration of 1 to approximately 5 cc oxygen/g $D_5W$, when the internal diameter of the distal tip of the hollow capillary tubing was less than approximately 7 microns.

In order to examine the effect of the infusion of the oxygen/$D_5W$ mixture on the oxygenation of blood and on blood element integrity, 20–33 cc's of citrated venous dog blood was placed in a beaker. The air above the blood was replaced with an inert gas such as helium, and the beaker was covered with paraffin. An Oximetrics oxygen saturation catheter for continuous monitoring of oxygen saturation was placed in the blood. A magnetic stirrer was used on the lowest setting to gently mix the blood, while the hollow silica capillary tubing was immersed in the blood before delivery of the oxygen/$D_5W$ mixture.

Typically, the oxygen saturation had a baseline level of 15% to 40%. The infusion was terminated when the oxygen saturation increased to 80% or greater. In all cases, the increase in oxygen saturation was commensurate with the quantity of oxygen delivered (calculated from the measured flow rate of $D_5W$ and the oxygen content of the fluid).

The i.d. of the capillary tubing at its distal end was measured by inspection under a light microscope coupled to video camera and color monitor at an overall magnification of approximately 1000×. Knowledge of the flow rate and i.d. of the tubing at its distal end permitted calculation of the velocity of flow at this location. The flow velocity was then compared against measurements of free plasma hemoglobin. The latter was determined, after centrifugation of blood elements, spectrophotometrically in the plasma (supernatant) by the absorption at 572 nm (a strong absorption peak of hemoglobin). The results are consistent with findings of other investigators who have noted that marked erythrocyte hemolysis occurs at flow velocities greater than 2,000 cm/sec. When flow velocity was less than 400 cm/sec, no evidence of hemolysis was found to occur.

Thus, it is possible to oxygenate blood without either bubble formation or erythrocyte hemolysis.

In one embodiment of this invention, a bundle of 25 fused silica capillary tubes, with an i.d. of 105 microns and an o.d. of 144 microns per tube, was drawn in a flame so that the o.d. of the bundle was sufficiently small to place within 30 micron to 150 micron i.d. fused silica capillary tubing. The length of the bundle was only a few millimeters in each case, and the bundle was bonded to the outer capillary tubing by annealing in a flame. Each small tubing, which now had an i.d. of approximately 5 microns, provided the same small bubbles and flow rate as the system described above, and the overall flow from the outer silica tubing was simply the sum of the individual tubes. Typically, a flow rate of at least 0.01 cc/min. can be achieved through a 5-7 micron (i.d.) tubing, so that the overall flow rate from the bundle of tubes was at least 0.25 cc/min. By use of an outer tubing with an i.d. of 150 microns, approximately 280 tubes with an i.d. of 6 microns can be positioned at the distal tip, and a flow rate of greater than 2 cc/min can be achieved with the outer tubing. Additional outer tubings with the bundle of small tubes can be added to achieve and level of flow desired.

In the relatively low oxygen yield system described above, wherein 2 to approximately 5 cc of oxygen per gram of $D_5W$ can be delivered, oxygen hydrate particles can be suspended to provide a much greater oxygen yield per gram of $D_5W$. At an oxygen concentration of 4-5 cc oxygen/g $D_5W$ at 0° C.–4° C., the concentration is sufficient to prevent any hydrate decomposition prior to exiting the capillary tubing. With the use of a Jet Pulverizer, it has been possible to grind ice to a mean particle size of 1-2 microns, and it should therefore be possible to grind a mixture of oxygen hydrate and ordinary $D_5W$ together to this same small dimension. The hydrate particles will remain solid under pressure (e.g., greater than 300 psi at 0° C.), while the ordinary $D_5W$ will provide a liquid carrier for the hydrate particles. The latter should pass easily through tubing having an i.d. of 3 to 7 microns.

The exiting stream at the distal end of the capillary tubing can be modified in many ways to enhance mixing, alter flow velocity, etc., so that uniform mixing with blood can be achieved without mechanical trauma to blood elements.

Further experiments with a strobe light source have provided further insight into oxygenation of blood. In one experiment, a 30 cc capacity Leco high pressure vessel was filled with 5 g % dextrose in water. Then a small volume of the latter (2 to 8 cc) was removed before connecting the vessel to a source of compressed oxygen, typically a standard oxygen cylinder at 1500 to 2500 psi, for a period of approximately 15 sec. The vessel was then isolated from the oxygen source, and the contents of the vessel were compressed by a piston driven by a hydraulic compressor to a pressure of 5,000 to 15,000 psi for 15 minutes or longer.

The high pressure forced all oxygen gas to be dissolved in the liquid, so that no bubbles were present. At the distal end of the vessel, a valve connected the latter to a high pressure sintered metal filter having an average pore size of 0.5 microns. A silica capillary tubing was mounted at its proximal end in a stainless steel capillary tube assembly which was connected to the distal end of the filter. The distal end of the capillary tubing, which had a typical internal diameter of 30 to 150 microns, had been drawn in a propane torch to an internal diameter of 2 to 25 microns. Alternatively, a 1-3 cm length of 5 micron i.d./140 micron o.d. silica tubing was epoxied within the distal end of 150 micron i.d. tubing. When the oxygenated liquid was forced through the silica capillary tubing, the greatest resistance to flow was at the distal end of this tubing, so that the pressure in the non-tapered end of the tubing was similar to that in the pressure vessel (5,000 to 15,000 psi). Because of the high resistance at the end of the silica tubing, the flow rate typically ranged from 0.002 cc to 0.05 cc per minute.

The fluid stream which emerged from the distal end of the tubing was viewed under a light microscope at either 100× or 400× magnification. A 20 nanosecond, broad spectrum strobe light (Model 437B High Intensity Nanopulse System, Xenon, Inc.) 37 froze" the motion of the stream, estimated to have a velocity of 100 to 4000 cm/sec. Photographic recordings were made on Tmax P3200 Kodak film in a camera mounted on the microscope. The stream was observed in air, under water, and finally under plasma.

The results of these studies demonstrated that, although bubbles were invariably present when the stream was viewed in air, as evidenced by growing droplet size, no bubbles were formed or were present in any portion of streams which were viewed under water or plasma, when the oxygen content of the liquid was approximately 5 cc per gram or less and the i.d. of the tapered distal end of the silica tubing was 7 microns or less.

For lower oxygen concentrations, on the order of 1 to 1.5 cc per gram, a larger i.d. (<25 microns) of the tapered end of the silica capillary tubing was used with no bubble formation. Stream velocity over a 100 to 4000 cm/sec range and driving hydraulic pressure over a 2,000 to 15,000 psi range had no effect on this observation.

Studies by other investigators (e.g., Hemmingsen E. A., *Cavitation In Gas-Supersaturated Solutions*, J. Applied Physics 1:213-218, 1975) have shown that water can be supersaturated to some degree with gases and, after hydraulic compression of the gas/water mixture at 0.5 to 1 kbar to dissolve all gas nuclei, a sudden release (over 2-3 seconds) of the pressure to 1 bar resulted, remarkably, in no immediate bubble formation. In the case of oxygen, the upper limit of gasification of water which did not result in bubble formation upon decompression was found to be approximately 140 psi, which corresponds to a gas concentration of about 4.2 cc oxygen per gram of water, and higher concentrations were achievable at temperatures below 3° C. If the fluid after decompression was disturbed in some manner, such as shaking or heating, bubble formation ensued.

When water is hydraulically compressed to 0.5 to 1.0 kbar, all bubbles and nuclei are forced to dissolve, and spontaneous bubble formation then requires that the molecular structure of water needs to be disrupted. When previous investigators attempted to explain why a greater gas concentration was not achievable without spontaneous cavitation upon release to 1 bar, it was felt that small density or thermal gradients in water allowed a small collection of gas molecules (a minimum of 10,000 gas molecules is thought to be necessary to overcome the surface tension of water at very small dimensions) to form. Once formed, rapid growth would then occur by diffusion from the water phase.

By analogy, it appears than, when 5 g% dextrose in water is supersaturated with oxygen to a concentration of approximately 5 cc per gram or less, stability of the gasified fluid is maintained despite ejection through a tubing, as long as the internal diameter of the tubing is sufficiently small. The present work demonstrates that supersaturated fluids can be subjected to 1 bar and movement at the above velocities without spontaneous cavitation, i.e., bubble formation, occurring. Why larger tubings result in bubble formation is unknown, but it is quite possible that density and thermal gradients within water are magnified, compared to smaller tubings, between different sites of a given cross-section of the flow field.

To summarize, I have shown that an oxygen supersaturated solution of 5 g % dextrose in water can be injected into water or plasma with no bubble formation. Although the oxygen content of this approach is limited to approximately 5 cc per gram, the oxygen content can be greatly increased by adding particles of a gas hydrate, such as oxygen hydrate particles. The latter should be completely stable, at 0° C. and >120 bar pressure, since the concentration of oxygen required in the liquid phase under equilibrium conditions is approximately 5 cc per gram. The hydrate particles, if sufficiently small (e.g., 1-3 microns in diameter), would produce short-lived bubbles upon ejection into blood and decomposition, while the liquid phase would produce no bubbles. In theory, a maximal oxygen content of as high as 100 cc per gram of injectate could be achieved with a 2:1 suspension of hydrate: water ($D_5W$).

Regional infusion of fluids supersaturated with oxygen into specific vascular spaces has utility even in the absence of hypoxemia.

Intraluminal infusion of oxygen-supersaturated crystalloids, such as 5 g % dextrose in water, into arterial blood which is already saturated with oxygen can be used to supersaturate blood without foam formation. Other techniques for enhancement of regional oxygen perfusion such as the use of hydrogen peroxide produce foam during decomposition into oxygen and water upon contact with tissue catalase: Foam formation blocks blood flow.

In a variety of clinical settings, regional infusion of oxygen-supersaturated crystalloids to supersaturate blood would be expected to have a beneficial response. For example, in patients with either acute myocardial infarction or a cerebrovascular accident, local infusion of the oxygen-supersaturated fluid directly into a coronary artery or a carotid artery would greatly enhance delivery of oxygen to ischemic tissue. The greater the oxygen content of blood, the greater will be the ability of plasma compared to red blood cells to perfuse ischemic tissue.

By analogy, placement of patients, suffering from either of these conditions, in a hyperbaric oxygen chamber reduces tissue ischemia more effectively than simply breathing oxygen at 1 bar. The resultant high partial pressures of oxygen as well as the high oxygen content of arterial blood into which the oxygen-enriched fluid is infused would simulate the beneficial effects of hyperbaric oxygen. The potential systemic toxicity, particularly pulmonary toxicity, would be avoided by the local intra-arterial infusion.

Regional intravascular infusion of oxygen-enriched crystalloids into tumors would also be expected to enhance the efficacy of radiation therapy, since oxygen radicals produced during the latter form the basis for subsequent tumor necrosis. There are undoubtedly many more examples of the potential utility of regional intravascular infusion of oxygen-enriched crystalloids, including enhancement of tissue responses to photodynamic therapy (e.g., hemotoporphyrin derivative, phthalocyanines, purpurins, etc.); treatment of myocardial failure with prolonged infusions; and potential treatment of chronic lesions such as tumors and atheromatous plaques which may resolve over a prolonged period of infusion as a result, for example, of improved oxidative catabolic activity of tissue macrophages.

What is claimed is:

1. A method of delivering oxygen into an environment of interest, such as blood or plasma, comprising the steps of:
   preparing a mixture of oxygen and a liquid;
   compressing the mixture so that the oxygen dissolves in the liquid to form an oxygen-enriched liquid;
   delivering the oxygen-enriched liquid to a catheter having an internal diameter and length which retains the oxygen in solution and prevents formation of bubbles in the oxygen-enriched liquid;
   positioning the catheter in the environment of interest; and
   injecting the oxygen-enriched liquid into the environment through the catheter so that no bubbles are formed, and the environment rapidly becomes enriched in oxygen.

2. The method of claim 1, wherein the liquid is water.

3. The method of claim 1, wherein the liquid is a physiologic crystalloid solution.

4. A method of delivering oxygen into an environment of interest, such as blood or plasma, comprising the steps of:
   preparing a mixture of oxygen and a liquid wherein the liquid is a physiologic crystalloid solution of 5% dextrose and water;
   compressing the mixture so that the oxygen dissolves in the liquid to form an oxygen-enriched liquid;
   delivering the oxygen-enriched liquid to a catheter having an internal diameter and length which retains the oxygen in solution and prevents formation of bubbles in the oxygen-enriched liquid;
   positioning the catheter in the environment of interest; and
   injecting the oxygen-enriched liquid into the environment through the catheter so that no bubbles are formed, and the environment rapidly becomes enriched in oxygen.

5. A method of delivering oxygen into an environment of interest, such as blood or plasma, comprising the steps of:
   providing a mixture of 1-6 cc of oxygen per gram of water;
   compressing the mixture so that the oxygen dissolves in the liquid to form an oxygen-enriched liquid;
   delivering the oxygen-enriched liquid to a catheter having an internal diameter and length which retains the oxygen in solution and prevents formation of bubbles in the oxygen-enriched liquid;
   positioning the catheter in the environment of interest; and
   injecting the oxygen-enriched liquid into the environment through the catheter so that no bubbles are formed, and the environment rapidly becomes enriched in oxygen.

6. The method of claim 1, wherein the step of compressing the mixture comprises applying a pressure of about 0.5 to 1 kbar.

7. A method of delivering oxygen into an environment of interest, such as blood or plasma, comprising the steps of:
preparing a mixture of oxygen and a liquid;
compressing the mixture so that the oxygen dissolves in the liquid to form an oxygen-enriched liquid;
passing the oxygen-enriched liquid through a filter for removing solid particulates to form a filtered liquid before delivery to a catheter;
delivering the filtered liquid to the catheter, the catheter having an internal diameter and length which retains the oxygen in solution and prevents formation of bubbles in the filtered liquid;
positioning the catheter in the environment of interest; and
injecting the filtered liquid into the environment through the catheter so that no bubbles are formed, and the environment rapidly becomes enriched in oxygen.

8. The method of claim 1, wherein the step of delivering the oxygen-enriched liquid to the catheter comprises providing a catheter having an internal diameter between 1-250 microns in size.

9. The method of claim 1, wherein the step of injecting the oxygen-enriched liquid into the environment of interest comprises injecting the liquid into the right atrium without any bubble formation so that no foam is formed and occlusion of pulmonary capillaries is circumvented.

10. The method of claim 1, wherein the step of injecting the oxygen-enriched liquid into the environment of interest comprises injecting the liquid into a great vein without any bubble formation so that no foam is formed and occlusion of pulmonary capillaries is circumvented.

11. The method of claim 1, wherein the step of preparing a mixture of oxygen and a liquid comprises the step of providing a mixture of oxygen hydrate particles so that excessive hydrate decomposition does not occur.

12. A method of delivering oxygen into an environment of interest, such as blood or plasma, comprising the steps of:
preparing a mixture of oxygen hydrate particles and a liquid;
compressing the mixture so that the particles at least partially dissolve in the liquid to form an oxygen-enriched liquid;
delivering the oxygen-enriched liquid to a catheter having an internal diameter and length which retains the oxygen in solution and prevents lasting formation of any bubbles which would otherwise emerge from the oxygen-enriched liquid upon emergence from the catheter;
positioning the catheter in the environment of interest; and
injecting the oxygen-enriched liquid into the environment through the catheter so that no bubbles are formed or disappear rapidly as a result of their small size and so that bubble coalescence does not occur, such that the environment rapidly becomes enriched in oxygen.

13. A method of gasification of an environment of interest having the characteristic of a low concentration of gas, comprising the steps of:
preparing a solid mixture of a gas hydrate and a carrier material;
compressing the solid mixture at a low temperature so that the gas hydrate does not prematurely liberate gas by decomposition; and
raising the temperature of the solid mixture while maintaining pressure so that the carrier material melts to form a suspension of particles of the gas hydrate in the carrier liquid;
delivering the suspension to a catheter having an internal diameter and length which retains at least a portion of the gas hydrate in suspension in the carrier liquid;
positioning the catheter in the environment of interest; and
injecting the suspension of particles of the gas hydrate into the environment through the catheter so that any bubbles formed disappear rapidly as a result of their small size and so that bubble coalescence does not occur, such that the environment rapidly becomes enriched in the gas.

14. The method of claim 1, wherein the step of injecting the oxygen-enriched liquid into the environment of interest comprises injecting the liquid into a lumen of a blood vessel which communicates locally with tissue.

15. The method of claim 14, wherein the tissue is myocardium.

16. The method of claim 14, wherein the tissue is a neoplasm.

17. The method of claim 14, wherein the tissue is within the central nervous system tissue.

18. The method of claim 14, wherein the tissue is infected with a micro-organism.

19. The method of claim 14, wherein the tissue is atheromatous plaque.

20. The method of claim 14, wherein the tissue is acutely hypoxic.

21. The method of claim 14, wherein the tissue is chronically hypoxic.

22. The method of claim 14, wherein the tissue is normoxic, but responds to treatment with oxygen delivery which exceeds normal levels.

23. The method of claim 14, wherein the oxygen-enriched liquid which is injected into the blood vessel mixes with native blood flow to the tissue.

24. The method of claim 14, wherein the oxygen-enriched liquid is injected distal to an inflated balloon which occludes the vessel and the oxygen-enriched liquid thereby displaces at least a portion of native blood flow to the tissue.

25. The method of claim 14, wherein injection of the oxygen-enriched liquid into the lumen of the blood vessel supersaturates the tissue with oxygen.

26. A method of delivering oxygen into an environment of interest, comprising the steps of:
preparing a mixture of oxygen and plasma;
compressing the mixture so that the oxygen dissolves in the plasma to form an oxygen-enriched plasma;
delivering the oxygen-enriched plasma to a catheter having an internal diameter in length which retains the oxygen and solution and prevents formation of bubbles in the oxygen-enriched plasma;
positioning the catheter in the environment of interest; and
injecting the oxygen-enriched plasma into the environment through the catheter so that no bubbles are formed, and the environment rapidly becomes enriched in oxygen.

27. The method of claim 1, wherein injection of the oxygen-enriched liquid into blood supersaturates the blood with oxygen without significant bubble formation.

* * * * *

UNITED STATES PATENT AND TRADEMARK OFFICE
CERTIFICATE OF CORRECTION

PATENT NO. : 5,407,426
DATED : April 18, 1995
INVENTOR(S) : James R. Spears

It is certified that error appears in the above-indentified patent and that said Letters Patent is hereby corrected as shown below:

Column 1, line 13, insert the following:

--This invention was made with Government support, under Contract No. R01 HL 33252, awarded by the National Institutes of Health. The Government has certain rights in the invention.--

Signed and Sealed this

Thirty-first Day of October 1995

Attest:

BRUCE LEHMAN

*Attesting Officer*     *Commissioner of Patents and Trademarks*